(12) United States Patent
De Linage et al.

(10) Patent No.: US 11,291,102 B2
(45) Date of Patent: Mar. 29, 2022

(54) CORONA EFFECT PLASMA DEVICE AND PLASMA REACTOR

(71) Applicant: AIRINSPACE S.E, Elancourt (FR)

(72) Inventors: Pierre De Linage, Boulogne Billancourt (FR); Stephen Lunel, Angervilliers (FR); Stéphane Châtenet, Elancourt (FR)

(73) Assignee: AIRINSPACE S.E., Elancourt (FR)

( * ) Notice: Subject to any disclaimer, the term of this patent is extended or adjusted under 35 U.S.C. 154(b) by 0 days.

(21) Appl. No.: 16/657,223

(22) Filed: Oct. 18, 2019

(65) Prior Publication Data

US 2020/0060018 A1 Feb. 20, 2020

Related U.S. Application Data

(63) Continuation-in-part of application No. PCT/EP2018/000214, filed on Apr. 20, 2018.

(30) Foreign Application Priority Data

Apr. 20, 2017 (FR) ...................................... 17/00439
Oct. 21, 2018 (FR) ...................................... 18/71306

(51) Int. Cl.
*H05H 1/48* (2006.01)
*B01D 53/38* (2006.01)
(Continued)

(52) U.S. Cl.
CPC ............... *H05H 1/48* (2013.01); *A61L 9/015* (2013.01); *A61L 9/22* (2013.01); *B01D 46/0027* (2013.01);
(Continued)

(58) Field of Classification Search
CPC ...... H05H 1/48; H05H 2001/48; H05H 1/471; A61L 9/015; A61L 9/22; A61L 2209/14; A61L 2209/212; A61L 2209/22; A61L 2/202; A61L 9/046; A61L 2/14; A61L 11/00; A61L 2202/11; A61L 2202/25; A61L 2209/16; B01D 46/0027;
(Continued)

(56) References Cited

U.S. PATENT DOCUMENTS

| 2005/0174062 A1 | 8/2005 | Tanaka et al. | |
| 2008/0170971 A1* | 7/2008 | Bergeron | B03C 3/016 422/171 |
| 2016/0111859 A1* | 4/2016 | Katano | F24F 8/192 361/230 |

FOREIGN PATENT DOCUMENTS

| EP | 2120254 A2 | 11/2009 |
| EP | 2213618 A1 | 8/2010 |

(Continued)

OTHER PUBLICATIONS

International Search Report, dated Aug. 14, 2018, from corresponding PCT application No. PCT/EP2018/000214.

*Primary Examiner* — Xiuyu Tai
(74) *Attorney, Agent, or Firm* — Nixon & Vanderhye (57) ABSTRACT

A corona plasma cell includes a polarized electrode and a ground electrode, including a cylinder and a porous film, with the cylinder having a low profile and the polarized electrode not entering the cylinder; a corona plasma dual element including a first cell, a second cell having such a structure, which first and second cell are symmetrically arranged; and finally a plasma reactor including a plurality of cells or dual elements.

13 Claims, 5 Drawing Sheets

(51) Int. Cl.
  *B01D 53/75* (2006.01)
  *B01D 53/76* (2006.01)
  *B01D 53/86* (2006.01)
  *B01D 46/00* (2022.01)
  *A61L 9/22* (2006.01)
  *A61L 9/015* (2006.01)
  *C01B 13/11* (2006.01)
  *B01D 53/32* (2006.01)
  *H05H 1/24* (2006.01)

(52) U.S. Cl.
  CPC ............. *B01D 53/32* (2013.01); *B01D 53/38* (2013.01); *B01D 53/75* (2013.01); *B01D 53/76* (2013.01); *B01D 53/8675* (2013.01); *C01B 13/115* (2013.01); *A61L 2209/14* (2013.01); *A61L 2209/212* (2013.01); *A61L 2209/22* (2013.01); *B01D 2255/2073* (2013.01); *B01D 2255/50* (2013.01); *B01D 2255/702* (2013.01); *B01D 2257/106* (2013.01); *B01D 2258/06* (2013.01); *B01D 2259/818* (2013.01); *B01D 2279/40* (2013.01); *C01B 2201/14* (2013.01); *C01B 2201/22* (2013.01); *H05H 1/47* (2021.05)

(58) Field of Classification Search
  CPC ........ B01D 53/32; B01D 53/38; B01D 53/75; B01D 53/76; B01D 53/8675; B01D 2255/2073; B01D 2255/50; B01D 2255/702; B01D 2257/106; B01D 2258/06; B01D 2259/818; B01D 2279/40; B01D 2257/206; B01D 2257/702; B01D 2257/404; C01B 13/115; C01B 2201/14; C01B 2201/22; C01B 13/11; C01B 2201/62; B01J 19/088; B01J 2219/0849; B01J 2219/0833; B01J 2219/0896; H01T 19/04; H01T 23/00; H01T 19/02; H01J 37/32009; H01J 37/32532; B60H 3/0078; F24F 8/192; F24F 8/40; F24F 2221/28; Y02A 50/20; Y02P 20/133
  See application file for complete search history.

(56) References Cited

FOREIGN PATENT DOCUMENTS

EP  2234462 A2  9/2010
FR  2818451 A1  6/2002

* cited by examiner

CORONA EFFECT PLASMA DEVICE AND PLASMA REACTOR

FIELD OF THE INVENTION

The present invention relates to the field of plasma emission by corona discharge, and more particularly to that of plasma reactors.

PRIOR ART

It is known to use a corona plasma device to produce, by corona discharge, a plasma and an ion flow. Such a device advantageously allows to produce a plasma for ionizing a fluid passing through the device. Such ionization has multiple and complementary features, for example, in the treatment of a fluid, such as air.

According to a first feature, ionization allows, by ion deposition, to charge a particle contained in the fluid. This thus-charged particle can advantageously be retained by an electrostatic filter, which can be arranged downstream of the device. According to another feature, ionization has a neutralizing action on pathogenic organisms, such as viruses, which can be carried in the fluid. According to yet another feature, ionization advantageously produces oxidizing chemical species useful for the decontamination of a mechanical filter, such as an activated carbon filter, which can be arranged downstream of the device.

Also, a corona plasma device, or a plasma reactor comprising a plurality of such devices, advantageously constitutes an upstream stage of a multi-filter fluid treatment means.

It is known, to produce a corona plasma device, to use a polarized electrode and a ground electrode, arranged opposite the polarized electrode, and to apply between these two electrodes a significant potential difference, in the order of several thousand volts. This creates a plasma as well as corona discharges producing ionic discharges. The ionization effect of the fluid is obtained by creating a fluid circulation that forces the fluid to pass through the plasma.

To obtain such a plasma, according to the corona effect, there are two known configurations: according to a first configuration, called a tip-plane configuration, a polarized electrode with a small radius of curvature is arranged perpendicular to a substantially planar ground electrode; according to another configuration, called a wire-cylinder configuration, a polarized wire electrode is arranged axially in a cylindrical ground electrode.

FR 2818451, from the same Applicant, proposes to combine these two configurations by using a needle-shaped polarized electrode and a ground electrode comprising a substantially planar wire mesh screen, arranged perpendicular to the polarized electrode and a cylinder surrounding the polarized electrode over its entire length. This device is traversed by the fluid in a direction parallel to the coinciding axis of the polarized electrode and the cylinder.

Improving a corona plasma device is always sought, in terms of ionization efficiency, reduction of the volume occupied, or even the electrical energy consumed.

SUMMARY OF THE INVENTION

A first object of the invention is directed to a corona plasma cell (11) comprising a substantially needle-shaped polarized electrode (12) and a ground electrode (13), arranged opposite the polarized electrode (12), comprising a cylinder (14) substantially centered on the polarized electrode (12), and a porous film (15) substantially plane perpendicular to the polarized electrode (12), wherein the cylinder (14) has a low profile,] and the polarized electrode (12) does not enter the cylinder (14).

A second object is directed to a corona plasma dual element (10) comprising a first corona plasma cell (11) as defined previously, comprising a first polarized electrode (12) and a first ground electrode (13), arranged opposite the first polarized electrode (12), a second corona plasma cell (21) as defined in any one of claim 1 or 2, comprising a second polarized electrode (22) and a second ground electrode (23), arranged opposite the second polarized electrode (22), wherein the first cell (11) and the second cell (21) are arranged symmetrically.

A third object is directed to a plasma reactor (30) comprising a plurality of corona plasma devices arranged side by side in a substantially planar arrangement, wherein the devices are cells (11) as defined previously, or the devices are dual elements as defined previously.

A forth object is directed to a plasma air cleaning device comprising:
  i) at least one source of electrical power;
  ii) at least one ionizer connected to the power source;
  iii) at least one filter downstream of the ionizer;
  iv) at least one catalyst downstream of the ionizer and the at least one filter downstream of the ionizer, which catalyst allows the decomposition of ozone; and
  v) at least one means of overpressurizing the air to ensure the flow of air from the ionizer to the catalyst;

Wherein the ionizer is a corona plasma cell (11) as defined previously or a dual elements as defined previously.

DETAILED DESCRIPTION OF THE INVENTION

The subject-matter of the invention is a corona plasma cell comprising a substantially needle-shaped polarized electrode and a ground electrode, arranged opposite the polarized electrode, comprising a cylinder substantially centered on the polarized electrode, and a porous film substantially plane perpendicular to the polarized electrode, wherein the cylinder has a low profile, preferably with a negligible height compared to its diameter, and wherein the polarized electrode does not enter the cylinder.

According to another characteristic, the porous film is arranged, relative to the polarized electrode, on the side opposite the cylinder.

The porous film is a surface allowing the passage of air with pores having a size ranging from 0.1 mm to 500 mm, preferably from 5 mm to 50 mm.

The thickness of the porous film is advantageously between 0.5 and 50 mm, preferably between 1 and 5 mm.

Advantageously, the porous film is a wire mesh, the meshes of which can have different shapes (square, diamond, etc.).

Also advantageously, the wire mesh in question is a sheet of expanded metal.

The subject-matter of the invention is also a corona plasma dual element comprising a first corona plasma cell as previously defined comprising a first polarized electrode and a first ground electrode, arranged opposite the first polarized electrode, a second corona plasma cell as previously defined comprising a second polarized electrode and a second ground electrode, arranged opposite the second polarized electrode, wherein the first cell and the second cell are arranged symmetrically (head-to-tail).

According to another characteristic, the first polarized electrode and the second polarized electrode are connected to a same first potential, and the first ground electrode and the second ground electrode are connected to a same second potential, different from the first potential.

According to another characteristic, the first potential is negative and the second potential is the ground.

Advantageously, the one or more polarized electrodes are connected to a negative potential and are referred to as discharge electrodes.

According to another characteristic, the first polarized electrode and the second polarized electrode are substantially needle-shaped and are supported by a conductive support connected to the first polarized electrode, the second polarized electrode and the first potential, which conductive support is preferably substantially planar.

According to another characteristic, the conductive support comprises a printed circuit comprising at least one conductor track connected to the first polarized electrode, the second polarized electrode and the first potential.

According to another characteristic, a polarized electrode is arranged into a metalized via drilled in said at least one conductor track.

According to another characteristic, the printed circuit comprises openings; preferably in its entirety excluding a narrow strip provided around said at least one conductor track.

According to another characteristic, the first polarized electrode and the second polarized electrode are axially aligned and are preferably made integral (that is to say one and the same part).

According to another characteristic, at least one of the first cell and the second cell is a cell according to one of the previous embodiments.

The subject-matter of the invention is also a plasma reactor comprising a plurality of corona plasma emission devices arranged side by side in a substantially planar arrangement, wherein the devices are cells according to one of the previous embodiments, or the devices are dual elements according to one of the previous embodiments.

According to another characteristic, the arrangement is a substantially square grid.

The subject-matter of the invention is also directed to a plasma air cleaning device comprising:
i) at least one source of electrical power;
ii) at least one ionizer connected to the power source;
iii) at least one filter downstream of the ionizer;
iv) at least one catalyst downstream of the ionizer and the at least one filter downstream of the ionizer, which catalyst allows the decomposition of ozone; and
v) at least one means of overpressurizing the air to ensure the flow of air from the ionizer to the catalyst;

Wherein the ionizer is a corona plasma cell (11) as defined previously or a dual elements as defined previously.

The generation of the ozone powerful oxidant by non-thermal plasma air treatment systems is of significant interest in that it can significantly improve the removal of residual pollutants after plasma treatment. Now, the presence of this ozone in the atmosphere at the end of these treatment systems generates a significant stress of the airways and is therefore problematic. Therefore, it is imperative to carry out a post-treatment to eliminate these toxic byproducts and more particularly ozone whose output concentration may exceed 100 ppm (v) (0.2 g/m$^3$). To do this, a catalyst is incorporated which is selected from activated carbon, zeolite or manganese oxide (MnO2) and which allows a very rapid decomposition of ozone and nitrogen oxides at room temperature.

In this case, it is preferred to use a catalyst in the form of a honeycomb substrate, for example aluminum, which is covered with manganese oxide. Typically such a honeycomb substrate should have a thickness of at least 10 mm to have sufficient efficiency in ozone neutralization.

With regard to the at least one filter located downstream of the ionizer (but upstream of the catalyst), it must be made of a material allowing to withstand the strongly oxidizing atmosphere resulting from the presence of quantity of ozone at the ionizer outlet.

Preferably, the filter will be made of mineral material such as glass or ceramic and, particularly preferably, the filter will be made of glass fiber. To be effective, said at least one filter must have a thickness of at least 10 mm, in particular of glass fibers Now, in addition to its filtration function, the filter advantageously also allows delimiting an oxidation space between the ionizer and the catalyst. In this space, the particles leaving the ionizer are trapped until their almost complete degradation due to their reaction with ozone.

To do this, said at least one filter has a height less than or equal to 100 mm, preferably less than or equal to 200 mm and, particularly preferably less than or equal to 300 mm.

Typically, the filter may comprise the superposition of at least two layers of mineral material, preferably at least three or four layers, and particularly preferably at least five or six successive layers of mineral material, typically glass fibers.

Each of these layers will have a thickness of at least 10 mm, preferably of at least 20 mm and particularly preferably of at least 30 mm. Now, each of these layers will have a thickness of less than 50 mm.

These layers may have a linear or a V-profile so as to increase the filtration/retention area.

With regard to the air overpressurizing means ensuring the air flow through the ionizer, and then through the filter to the catalyst, it can take the form of a fan, a turbine. Preferably, this air overpressurizing means is a turbine.

Other characteristics, details and advantages of the invention will become apparent from the detailed description given below for information purposes in relation to the drawings.

Figure 1:
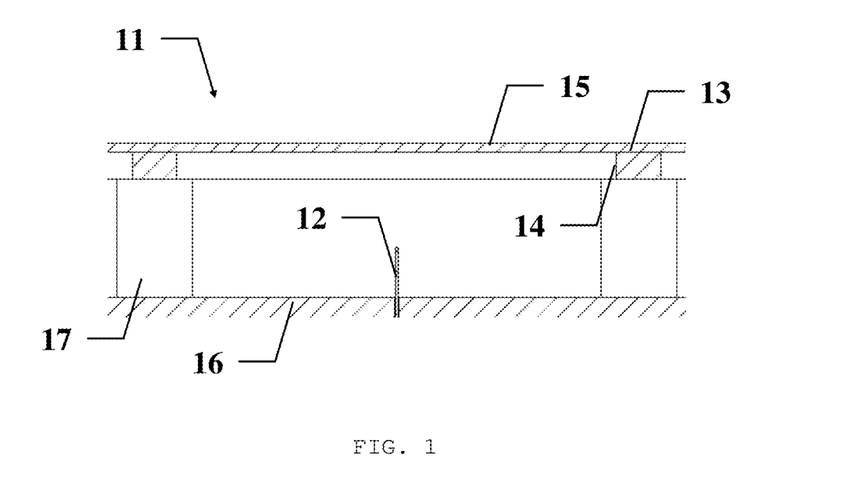
FIG. 1 illustrates, in a cross-sectional profile view, a cell according to the invention.

According to a first aspect, illustrated in FIG. 1, the invention relates to an improved corona plasma cell 11. In a known manner, such a cell 11 comprises a substantially needle-shaped polarized electrode 12 and a ground electrode 13, arranged opposite the polarized electrode 12. The ground electrode 13 comprises a cylinder 14 substantially centered on the polarized electrode 12 and a porous film 15 substantially plane perpendicular to the polarized electrode 12. The polarized electrode 12 is typically fixed on a support 16 advantageously perforated for allowing the passage of a fluid flow. The distance between the polarized electrode 12 and the ground electrode 13 is maintained by at least one spacer 17.

From FR 2818451, it is known to form such a ground electrode with a cylinder, substantially centered on the polarized electrode, of a high height in order to surround the polarized electrode over its entire length.

A cell 11 according to the invention is improved in that the cylinder 14 is shaped so as to have a low profile. This means that the height of the cylinder 14 is negligible compared to its diameter. Thus, the value of the cylinder diameter is of at least twice, preferably at least 3 or 5 times, and particularly at least 10 times the value of the cylinder height. Typically, the diameter of the cylinder is between 20 and 100 mm, preferably between 25 and 75 mm, for example between 30 and 60 mm and, particularly preferably between 35 and 55 mm. As for the thickness of the cylinder, it is less than 10 mm, preferably between 1 and 5 mm. In addition, the polarized electrode 12 is shaped short enough so that it does not penetrate the cylinder 14.

The flow of fluid to be ionized by means of the cell 11 is substantially vertical relative to FIG. 1.

The combined reduction in the height of the cylinder 14 and in the length of the polarized electrode 12 advantageously allows to drastically reduce the overall height of the cell 11, since the ground electrode 13, which is much lower, can be brought closer to the polarized electrode 12, which is itself shortened. This advantageous allows to obtain a cell 11, or any system based on such a cell 11, such as a plasma reactor 30, with a thickness, and therefore an overall size, in the direction of the fluid flow, that is significantly reduced.

Keeping the polarized electrode 12 out of the cylinder 14 allows the plasma to be shaped substantially in a very flattened cone shape, substantially transverse to the fluid flow, promoting good ionization.

Thus, according to an embodiment, for a distance d between the tip of the needle and the porous film, and a cylinder diameter between 2d and 5d, with an optimum at 3d, the opening angle of the ion flow cone is between 136° and 112°.

According to another characteristic, still illustrated in FIG. 1, the porous film 15 is arranged, relative to the discharge electrode 12, on the side opposite the cylinder 14. This is advantageous for the shape of the plasma/ion flow. In addition, this simplifies manufacturing, since a continuous porous film 15 can be placed behind the cylinder 14, while the porous film 15 is only visible from the polarized electrode 12 in the inner circular opening defined by the cylinder 14.

Figure 2:
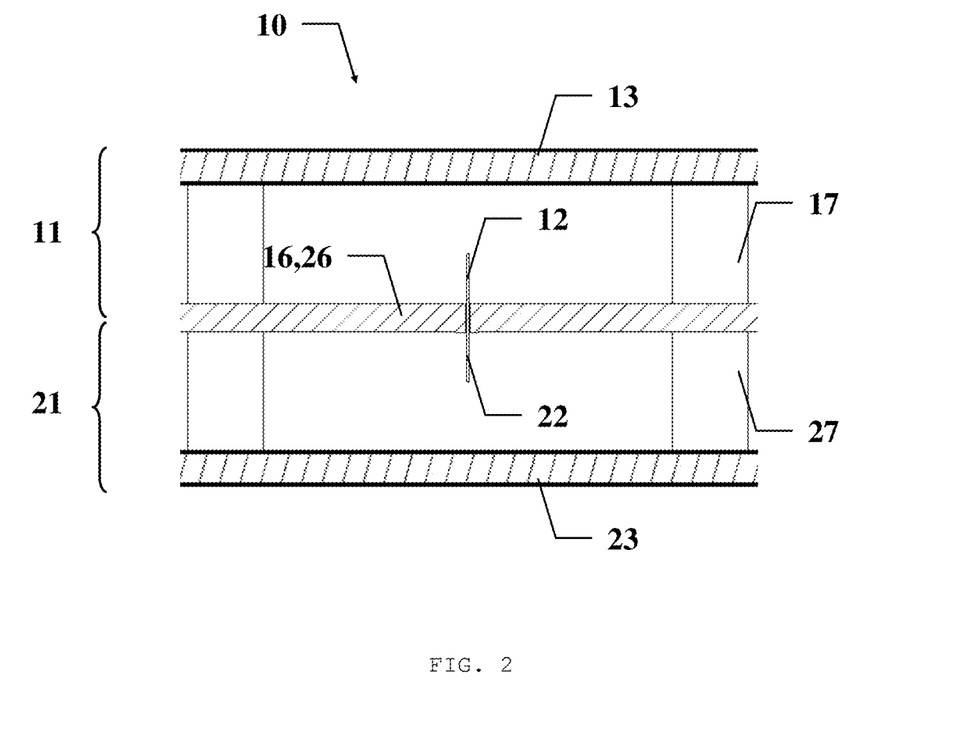
FIG. 2 illustrates, in a cross-sectional profile view, a dual element according to the invention.

According to another aspect, more particularly illustrated in FIG. 2, the invention also relates to an advantageous configuration, wherein two cells 11,21 are assembled symmetrically (in a head-to-tail or inverted configuration). Also, the invention relates to a corona plasma dual element 10 comprising a first corona plasma cell 11 and a second corona plasma cell 21. The first cell 11 comprises a first polarized electrode 12 and a first ground electrode 13, arranged opposite the first polarized electrode 12. The second cell 21 comprises a second polarized electrode 22 and a second ground electrode 23, arranged opposite the second polarized electrode 22.

Figure 3:
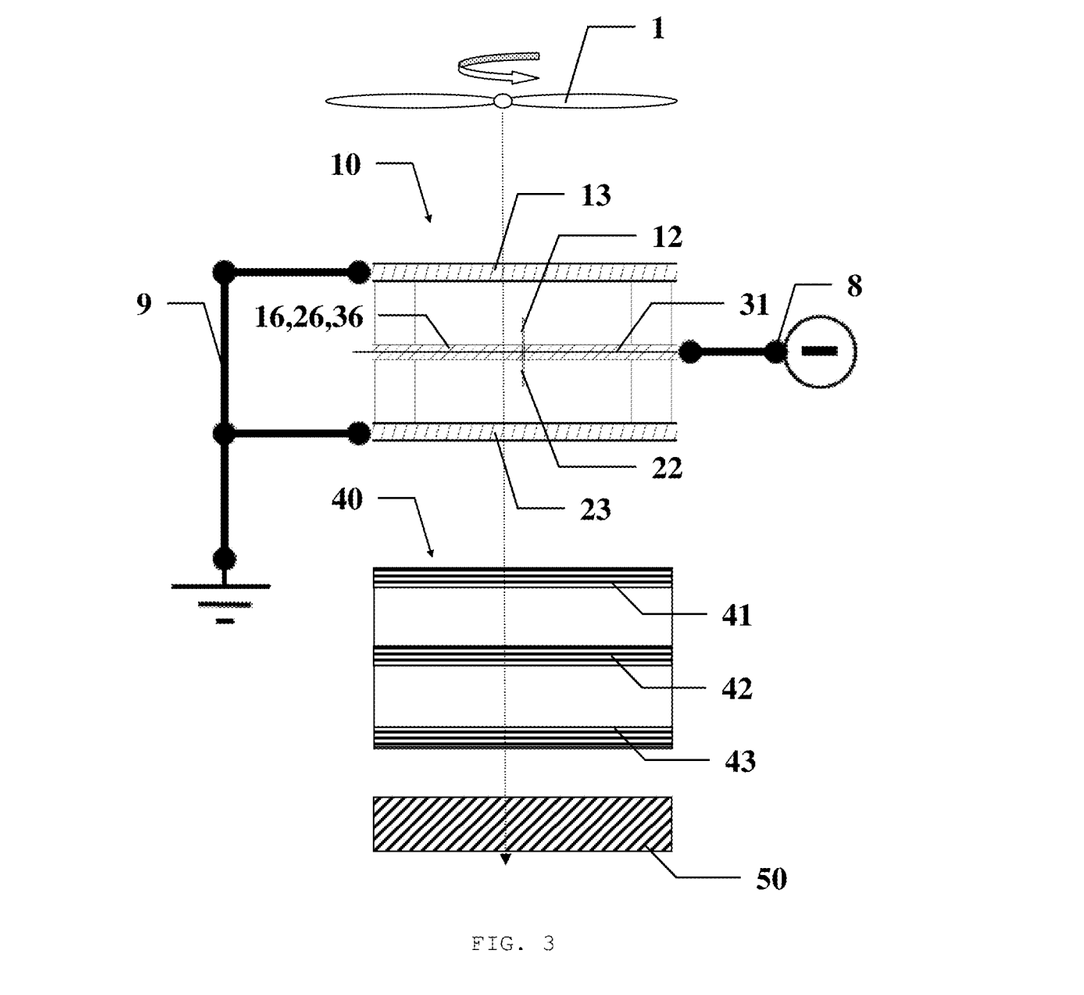
FIG. 3 illustrates, in a cross-sectional profile view, a plasma air cleaning device according to the invention.

According to another characteristic, more particularly illustrated in FIG. 3, the invention relates to a plasma air cleaning device comprising a ionizer (10) as represented in FIG. 3. Such a device comprise an air overpressurizing means (1) corresponding to a fan (1), which ensures the air flow in the device, first in the ionizer (10), then in the filter (40) comprising successive layers of glass fibers (41,42, 43), and finally in the catalyst (50) to allow ozone to be removed from the outlet effluents. The ionizer comprises two inverted and contiguous cells with a polarized electrode (12,12), and a ground electrode (13,23). The first polarized electrode 12 and the second polarized electrode 22 are connected to a same first potential 8, and the first ground electrode 13 and the second ground electrode 23 are connected to a same second potential 9, different from the first potential 8.

The signs of the first and second potentials 8,9 can be any signs. However, it is known that ionization obtained by corona effect is more effective when the polarized electrode is connected to a negative potential (called a discharge electrode). Also, preferably, the first potential 8 is negative and the second potential 9 is the ground.

It was found that a symmetrical arrangement of the first cell 11 and the second cell 21 (preferably in a head-to-tail configuration) had many non-obvious advantages. Other advantages are also obtained with a same polarization of the two cells 11,21.

Doubling the cells 11,21 allows to significantly improve the efficiency obtained. In addition, it has been shown that the lifetime of a dual element 10 is significantly increased relative to a single cell 11. Indeed, an adverse effect of a corona cell is that its polarized electrode 12,22 precipitates dielectric crystals which, by gradually isolating said polarized electrode 12,22, reduce the efficiency of the cell 11,21. Using two cells instead of one has allowed to significantly improve the lifespan of the reactor 30.

Since the first cell 11 has an orientation opposite to that of the second cell 21, their ionizing effects combine and complement each other, thus increasing the overall ionizing effect.

The opposite orientation also allows to apply a same polarization to both cells 11,21.

These two combined orientation and polarization characteristics allow to advantageously fix the first polarized electrode 12 on a first support 16 and the second polarized electrode 22 on a second support 26. Advantageously, these two supports 16,26 can be a single common support 36, with the polarized electrodes 12,22 supported by one face of the support 36, respectively.

This advantageously allows, since the polarity of the first polarized electrode 12 and the second polarized electrode 22 are the same (preferably negative), to use a common connector, as well as a common potential source, to polarize these two polarized electrodes 12,22. This structure is therefore particularly economical and advantageous.

Thus, according to an advantageous embodiment, the common support 36 can be conductive and connected to the first polarized electrode 12, the second polarized electrode 22 and the first potential 8.

According to another advantageous embodiment, the common support 36 comprises a printed circuit board comprising at least one conductor track 31 connected to the first polarized electrode 12, the second polarized electrode 22 and the first potential 8.

The polarization of a corona plasma device requires a significant potential difference between the polarized electrode and the ground electrode, which potential difference is in the order of several thousand volts. Also, the first potential 8 is very high and could be dangerous for an operator. The configuration according to the invention advantageously ensures that this first potential 8 is confined in the middle of the dual element 10. The high first potential 8 is therefore beyond the reach of an operator. Such a dual element 10, and therefore a reactor 30 built based on such a dual element 10, have a naturally safe conformation in view of this electrical risk.

Since the support 16,26 is a printed circuit board, with the first potential 8 distributed within the support by means of a conductor track 31, advantageously arranged in said printed circuit board, according to another characteristic, a substantially needle-shape polarized electrode 12,22 is advantageously assembled on the support 16,26 by means of a via 33 drilled in the printed circuit board. This advantageously allows the polarized electrode 12,22 to be fixed by means of welding. Advantageously, the via 33 is metalized and drilled into a conductor track 31. The drilling is such that it ensures the electrical connection. Thus, fixing the polarized electrode 12,22 into the via 33 in a connected manner ensures the connection between the polarized electrode 12,22 and the first potential 8. This allows a simple embodiment of fixing and connecting the polarized electrode 12,22.

The printed circuit board that is arranged across the fluid flow is advantageously perforated to allow the passage of this fluid flow. According to an embodiment, at least one opening 38 is made for this purpose. In order to maximize the passage of fluid through it, said at least one opening 38 can cover the entire surface of the printed circuit board excluding at least one narrow strip provided around said at least one conductor track 31.

Figure 8:
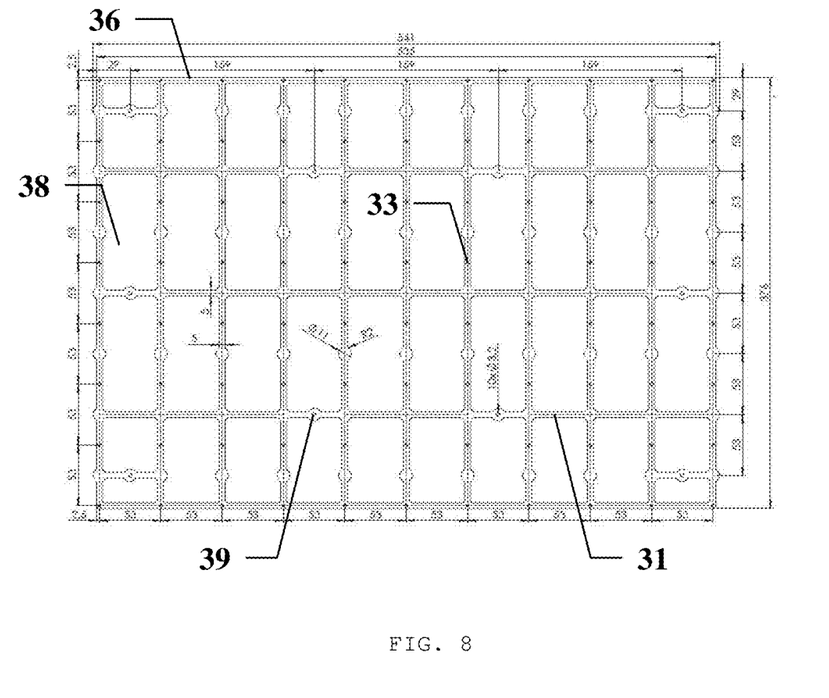
FIG. 8 illustrates, in a view from above, a printed circuit supporting polarized electrodes.

An embodiment of a printed circuit board for a plasma reactor according to this characteristic is illustrated in FIG. 8.

In the above description, the relative position of the first polarized electrode 12 and the second polarized electrode 22 was arbitrary. According to another advantageous characteristic, as illustrated in FIGS. 1-6, the first polarized electrode 12 and the second polarized electrode 22 are axially aligned. This advantageously allows to make them integral, with a single needle with two tips simultaneously forming two polarized electrodes 12,22. This also advantageously allows to fix the two polarized electrodes 12,22 simultaneously in a same through via 33, in a single operation.

Figure 4:
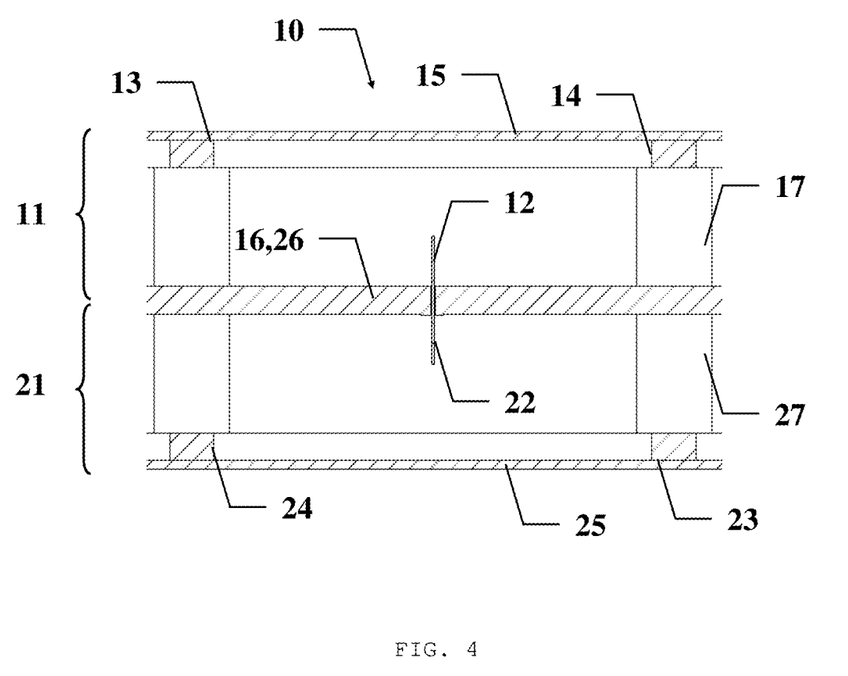
FIG. 4 illustrates, in a cross-sectional profile view, a dual element comprising two cells from FIG. 1.
Figure 5:
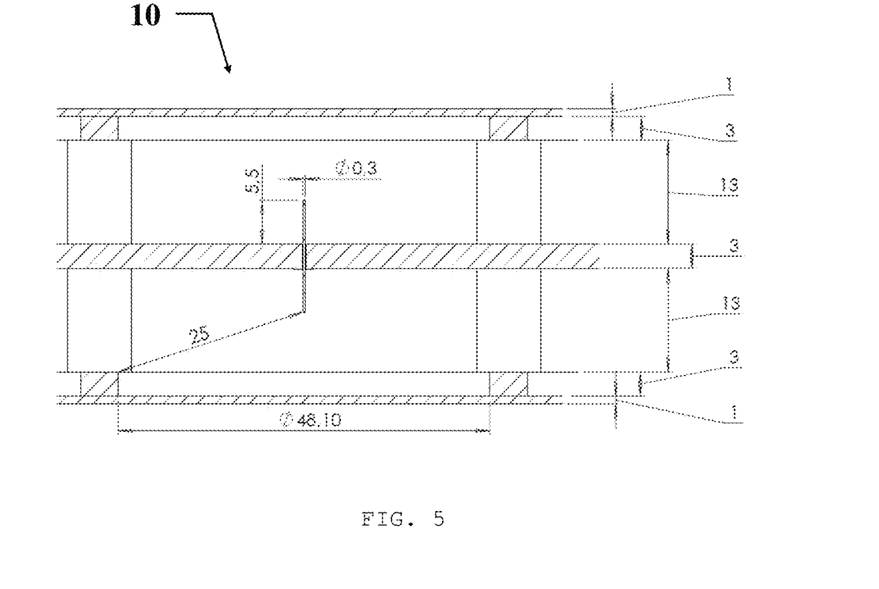
FIG. 5 illustrates, in a cross-sectional profile view, the dual element from FIG. 4 dimensioned according to an embodiment.
Figure 6:
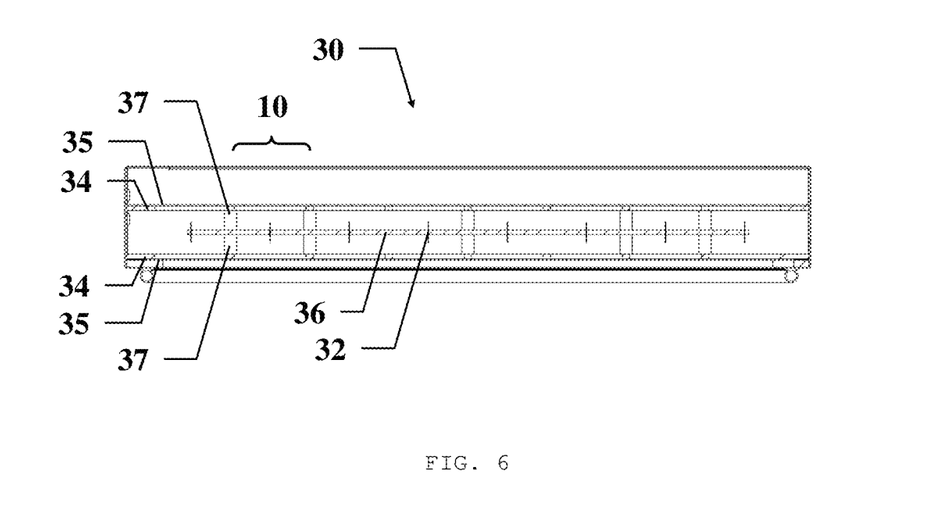
FIG. 6 illustrates, in a cross-sectional profile view, a plasma reactor.

In a dual element 10, the two cells 11,21 can be of any type. According to an advantageous embodiment, the first cell 11, the second cell 21, or both are a cell according to the invention, as illustrated in FIG. 1, namely a cell with a cylinder 14 with a low profile. FIGS. 4-6 illustrate a configuration with two such identical cells.

Based on a cell 11 or a dual element 10 according to one of the previous embodiments, it is possible to build a plasma reactor 30. The known principle of a plasma reactor is to juxtapose, in a side-by-side arrangement, in a plane perpendicular to the fluid flow, a plurality of corona plasma devices. This allows to increase at will the cross-section and therefore the flow rate of fluid that can pass through the plasma reactor 30.

According to another aspect of the invention, a plasma reactor 30 juxtaposes devices that are cells 11, according to one of the previous embodiments, or dual elements 10 according to one of the previous embodiments.

Figure 7:
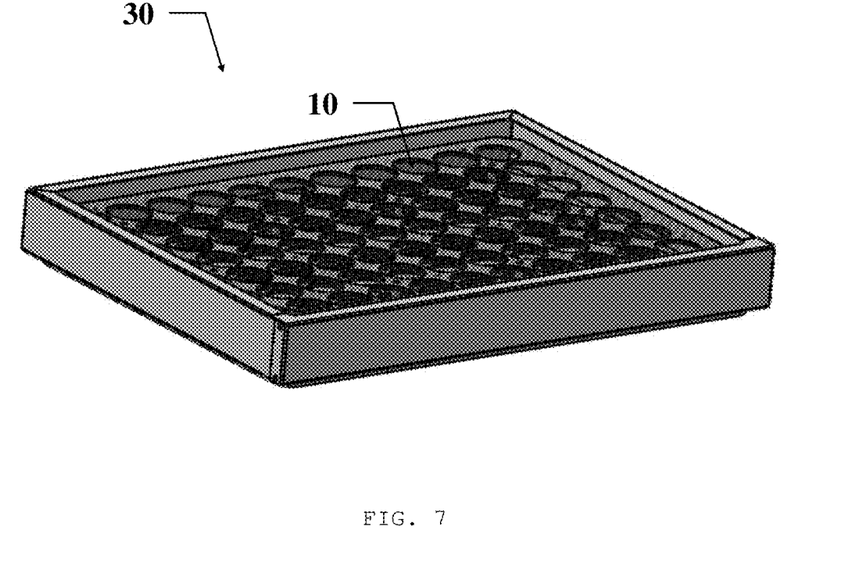
FIG. 7 illustrates, in a perspective view, a plasma reactor.

Such a plasma reactor 30, based on a dual element 10 comprising two cells 11 with a low profile cylinder 4, is illustrated in FIGS. 6 and 7.

Obtaining such a plasma reactor 30 is simplified by the choices made for obtaining a cell 11 or a dual element 10.

Thus, as shown in FIG. 6, a central printed circuit board serves as a support on both its faces for the two series of polarized electrodes 32. It also ensures, by means of conductor tracks 31, that these polarized electrodes 32 are connected to the first potential 8 (preferably negative). A series, respectively two series, of spacers 37 move(s) away and support(s) one drilled plate, respectively two drilled plates, 34, of cylinders and one plate, respectively two plates, 35, of a porous film. The plates 34,35 are advantageously metallic in order to be conductive and connected to the second potential 9.

The arrangement of the devices 1,10 within a plasma reactor 30 can be any arrangement. However, an optimization of both the ionization function and the volume occupied is sought. Also the cell 11/dual element 10 density is advantageously important. The impression in the plane of a cell 11 or a dual element 10 comprising a cylinder 14,24 is circular. Also, a hexagonal or grid arrangement, for example a square, is advantageous.

FIG. 8 illustrates a possible embodiment of a printed circuit board adapted for such a square grid arrangement. This printed circuit board comprises an array, for example a rectangular array, of conductor tracks 31. These tracks are advantageously embedded in the insulating thickness of the printed circuit board. They are electrically connected to the first potential 8. In a substantially square grid arrangement, vias 33 are drilled, into which the polarized electrodes 12,22,32 are installed. The printed circuit board is cut with openings 38 occupying a maximum surface area in order to maximize the fluid flow cross-section. This maximum surface area is only limited by saving a narrow strip around the tracks 31. Holes 39 are provided, advantageously without an electrical connection, in a spatially distributed manner, allowing the spacers 17,27,37, advantageously integrally made, to be fixed.

The invention claimed is:
1. A corona plasma dual element (10), comprising:
a first corona plasma cell (11), which includes a first polarized electrode (12), and a first ground electrode (13) arranged opposite the first polarized electrode (12); and
a second corona plasma cell (21), which includes a second polarized electrode (22), and a second ground electrode (23) arranged opposite the second polarized electrode (22),
wherein each of said first polarized electrode (12) and said second polarized electrode (22) are needle-shaped, and
wherein each of said first ground electrode (13) and said second around electrode (23) comprise
a cylinder (14) having a height and a diameter that is at least 3 or 5 times the height, and which is centered on the polarized electrode (12), the polarized electrode (12) not entering the cylinder (14), and
a porous film (15) extending along a plane perpendicular to the polarized electrode (12), said porous film being formed as a wire mesh, being arranged on a side opposite the cylinder (14) relative to the polarized electrode (12), and having a surface allowing passage of air with pores having a size ranging from 0.1 mm to 500 mm,
and wherein the first corona plasma cell (11) and the second corona plasma cell (21) are arranged symmetrically in an inverted configuration with the first polarized electrode (12) and the second polarized electrode (22) being made integral corresponding to a single needle with two tips simultaneously forming the two polarized electrodes (12, 22), said single needle being supported by and connected to a conductive support.

2. The dual element (10) of claim 1, wherein the first polarized electrode (12) and the second polarized electrode (22) are connected to a same first potential (8), and the first ground electrode (13) and the second ground electrode (23) are connected to a same second potential (9), different from the first potential (8).

3. The dual element (10) of claim 2, wherein the first potential (8) is negative and the second potential (9) is the ground.

4. The dual element (10) of claim 1, wherein the conductive support is a printed circuit board (PCB) comprising at least one conductor track (31) connected to the first polarized electrode (12), the second polarized electrode (22) and the first potential (8).

5. The dual element (10) of claim 4, wherein the polarized electrodes (12,22) are arranged into a metalized via (33) drilled in said at least one conductor track (31).

6. The dual element (10) of claim 4, wherein the PCB (36) comprises openings (38).

7. A plasma reactor (30) comprising a plurality of corona plasma devices arranged side by side in a planar arrangement, wherein the devices are cells (11) of claim 1.

8. The plasma reactor (30) of claim 7, wherein the arrangement is a square grid.

9. The dual element of claim 6, wherein the PCB comprises openings (38) in its entirety excluding a narrow strip provided around said at least one conductor track (31).

10. A plasma air cleaning device, comprising:
i at least one source of electrical power;
at least one ionizer connected to the power source;
at least one filter downstream of the ionizer;
at least one catalyst downstream of the ionizer and the at least one filter downstream of the ionizer, said catalyst configured to allow decomposition of ozone; and
}—at least one fan or turbine for overpressurizing the air to ensure flow of air from the ionizer to the catalyst, wherein the ionizer is the corona plasma dual element as defined in claim 1.

11. The plasma air cleaning device of claim 10, wherein the catalyst (50) is selected from the group consisting of: activated carbon, zeolite, and manganese oxide ($MnO_2$).

12. The plasma air cleaning device of claim 10, wherein the at least one filter downstream of the ionizer is made of a material resistant to an oxidizing atmosphere resulting from a presence of ozone in the outlet of the ionizer (10).

13. The corona plasma dual element of claim 1, wherein a diameter of each plasma cell is at least 10 times the height of the cylinder.

* * * * *